| United States Patent [19] | [11] Patent Number: 4,973,787 |
| Colvin | [45] Date of Patent: Nov. 27, 1990 |

[54] PROCESS FOR THE THERMAL DIMERIZATION OF ISOPRENE

[75] Inventor: Howard A. Colvin, Tallmadge, Ohio

[73] Assignee: The Goodyear Tire & Rubber Company, Akron, Ohio

[21] Appl. No.: 402,366

[22] Filed: Sep. 5, 1989

[51] Int. Cl.$^5$ .................................................. C07C 2/02
[52] U.S. Cl. ........................................ 585/508; 585/5
[58] Field of Search .................................... 585/5, 508

[56] References Cited

U.S. PATENT DOCUMENTS

| 4,033,829 | 7/1977 | Higgins, Jr. et al. | 203/9 |
| 4,086,147 | 4/1978 | Watson | 203/9 |
| 4,105,506 | 8/1978 | Watson | 203/9 |
| 4,182,658 | 1/1980 | Watson | 585/5 |
| 4,389,285 | 6/1983 | Douglas et al. | 585/5 |

FOREIGN PATENT DOCUMENTS 2421820  5/1974  Fed. Rep. of Germany .

*Primary Examiner*—Curtis R. Davis
*Attorney, Agent, or Firm*—Bruce J. Hendricks

[57] ABSTRACT

The present invention relates to an improved process for the thermal dimerization of isoprene. In particular, the present process involves heating isoprene at a temperature of from about 110° C. to about 250° C. in the presence of dinitrocresol. The present process is characterized by reduced amounts of polymer product and increased yields of isoprene dimer.

12 Claims, No Drawings

PROCESS FOR THE THERMAL DIMERIZATION OF ISOPRENE

FIELD OF THE INVENTION

This invention relates to a process for the thermal dimerization of isoprene at a temperature of from about 110° C. to about 250° C. in the presence of sufficient dinitrocresol to inhibit isoprene polymerization.

BACKGROUND OF THE INVENTION

Isoprene is a reactive diene that can undergo a variety of reactions including thermal dimerization. The first report of the thermal dimerization of isoprene was recorded in the late 1800's. In the absence of air or peroxides, only cyclic dimers are formed in the thermal dimerization of isoprene. Six cyclic dimers are formed.

TABLE I

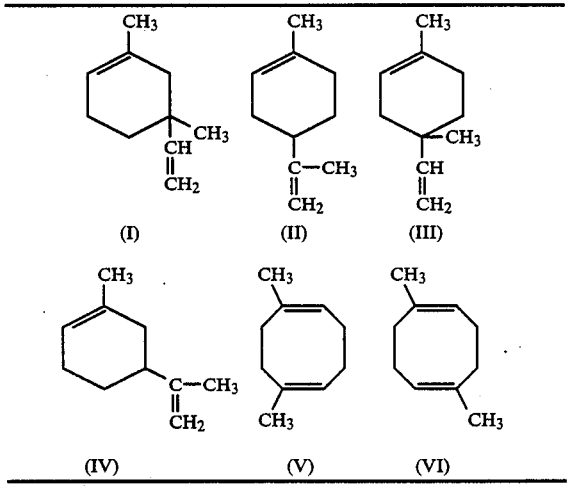

They are 1,5-dimethyl-5-vinyl-1-cyclohexene (I), 1-methyl-4-isopropenyl-1-cyclohexene, also known as limonene (II), 1,4-dimethyl-4-vinyl-1-cyclohexene (III), 1-methyl-5-isopropenyl-1-cyclohexene, also known as diprene (IV), 2,5-dimethyl-1,5-cyclooctadiene (V) and 1,5-dimethyl-1,5-cyclooctadiene (VI). The relative amounts of the six dimers are dependent on the reaction conditions. When the thermal dimerization is conducted at temperatures ranging from about 100°–190° C., dimers 1-methyl-4-isopropenyl-1-cyclohexene and 1-methyl-5-isopropenyl-1-cyclohexene (diprene) constitute 57% to 80% of the dimer product.

One major problem with the thermal dimerization of isoprene at high temperatures is that much of the isoprene is lost to the formation of polymer. A number of inhibitors have been tried to reduce polymer formation with various degrees of success. For example, G. Solomon, et al, Rubber Chemistry and Technology, 22, 956 (1949) disclose that isoprene dimerized in the presence of 10,000 ppm of picric acid at 200° C. produced 32% by weight polymer. J. Binder, et al., J. Poly. Sci., 38, 229 (1959) disclose isoprene dimerized in the presence of 1000 ppm of hydroquinone at 227° C. produced 10.8 weight percent polymer. German DE No. 2,421,820 discloses that a blend of 4000 ppm sodium nitrosylpentacyanoferrate/50 ppm t-butylcatechol has been used to reduce isoprene polymerization to as low as 0.5% at 150° C. during dimerization.

Limonene, also known as 1-methyl-4-isopropenyl-1-cyclohexene occurs in various oils, and particularly in the oils of lemon, orange, caraway, dill and bergamot. Although limonene can be produced from the thermal dimerization of isoprene, it is generally isolated from the peels of citrus fruits, so the price can fluctuate dramatically depending on how large the citrus crop is. Limonene is commonly used as a solvent, wetting and dispersing agent or as a component in high softening, water white tackifying resins. Since there are a number of commercial applications of limonene, but there being no consistent and economical way to produce it, there is a significant need for a cheap and dependable process to provide limonene in good yields.

SUMMARY OF THE INVENTION

The present invention relates to a process for the thermal dimerization of isoprene comprising heating isoprene at a temperature of from about 110° C. to about 250° C. in the presence of dinitrocresol.

DETAILED DESCRIPTION OF THE PREFERRED EMBODIMENT

The present invention relates to a process for inhibiting polymerization reactions during the thermal dimerization of isoprene. The isoprene is heated to a temperature of from about 110° C. to about 250° C. in the presence of the polymerization inhibitor. Preferably, the isoprene is heated to a temperature of about 175° to about 200° C.

The polymerization inhibitor for use in the present invention is a dinitrocresol. More specifically, the dinitrocresol may be 3,5-dinitro-o-cresol, 4,6-dinitro-o-cresol or 2,6-dinitro-p-cresol. Preferably, the 4,6-dinitro-o-cresol is used because it is commercially available. The dinitrocresol should polymerization of the isoprene. Generally speaking, the concentration of the dinitrocresol may range from about 25 to about 3000 ppm with a range of from about 100 ppm to 1000 ppm. A preferred range of dinitrocresol is from about 50 to about 1000 ppm.

Generally speaking, the thermal dimerization of the isoprene is conducted under conditions known to those skilled in the art. The pressure of the reaction may vary but is generally conducted in a range of from about 300 psi (1551 cm of Hg at 0° C.) to about 600 psi (3100 cm of Hg at 0° C.).

The products from the thermal dimerization process of the present invention generally comprise six components. The largest two components are 1-methyl-5-isopropenyl-1-cyclohexene (diprene) and limonene (1-methyl-4-isopropenyl-1-cyclohexene). The other four components are 1,5-dimethyl-5-vinyl-1-cyclohexane, 1,4-dimethyl-4-vinyl-1-cyclohexane, 2,5-dimethyl-1,5-cyclooctodiene and 1,5-dimethyl-1,5-cyclooctadiene. Generally speaking, the yield of limonene may range of from about 25 to about 35% by weight of the overall dimer product.

The present invention may be conducted in a batchwise, semi-continuous or continuous manner.

The following examples are provided to illustrate the present invention although it should be understood that the invention is not limited to these specific examples. Percentages are by weight unless stated otherwise.

EXAMPLE 1

2,4-dinitro-o-cresol was dissolved into 408 grams (6 moles) of freshly distilled isoprene and charged to a one liter autoclave. The solution was flushed with nitrogen and heated to reaction temperature. The amounts of dinitrocresol was varied in each run and are provided in Table II below. The reaction times were measured from the point the reactor reached operating temperature. After the reaction was completed, the autoclave was cooled and the reactive mixture was distilled at atmospheric pressure. Isoprene was collected at 32° C. and the dimer cut was collected at an overhead temperature of 168°-174° C. The fractions and pot residue were weighed and the isoprene weight was adjusted to reflect any shortage in the material balance. Material balances were typically 95%. The dimer cut was analyzed by gas chromatograph using a DB-1701 capillary column.

Table II below lists the data from the five runs wherein a concentration of 1000 ppm, 500 ppm, 250 ppm, 125 ppm and 50 ppm of dinitrocresol was used at 175° C. with a reaction time of 90 minutes.

TABLE II

Effectiveness of DNC Inhibitor at 175° C./90 Min.

| Concentration DNC | % Isoprene Conversion | Selectivity to Dimer | % Polymer |
|---|---|---|---|
| 1000 ppm | 67.9 | 97.2 | 1.8 |
| 500 ppm | 66.7 | 92.6 | 5.1 |
| 250 ppm | 67.3 | 88.6 | 7.8 |
| 125 ppm | 67.7 | 86.2 | 8.8 |
| 50 ppm | 71.8 | 84.6 | 11.1 |

The chromatograph of the isoprene dimer cut identified six components shown in Table I. Table III below shows that the largest two components are diprene (1-methyl-5-isopropenyl-1-cyclohexene) and limonene (1-methyl-4-isopropenyl-1-cyclohexene).

TABLE III

| Component | % of Dimer Composition |
|---|---|
| Diprene | 33.6 |
| Limonene | 29.1 |
| 1,4-dimethyl-4-vinyl-1-cyclohexene | 18.6 |
| 1,5-dimethyl-5-vinyl-1-cyclohexene | 9.2 |
| 2,5-dimethyl-1,5-cyclooctadiene | 5.2 |
| 1,5-dimethyl-1,5-cyclooctadiene | 4.2 |

EXAMPLE 2 the procedure of Example 1 was reproduced with the exception that 1000 ppm of 2,4 dinitro-o-cresol was used and the reaction temperature and reaction time was varied. Table IV lists the data resulting from six runs.

TABLE IV

Polymer Formation as a Function of Temperature and Conversion (1000 ppm DNC)

| Rxn Temp. | Rxn Time (minutes) | Isoprene Conversion | Selectivity To Dimer | % Polymer |
|---|---|---|---|---|
| 175° C. | 60 | 58.0 | 98.1 | 1.0 |
| 175° C. | 90 | 67.9 | 97.2 | 1.8 |
| 175° C. | 120 | 69.4 | 97.1 | 2.0 |
| 175° C. | 150 | 72.6 | 96.7 | 2.1 |
| 200° C. | 60 | 83.1 | 96.7 | 2.2 |
| 200° C. | 90 | 87.8 | 97.3 | 2.3 |

The effect of dinitrocresol on polymer formation as a function of isoprene conversion and temperature is seen in Table IV above. At 175° C. only 2.1% polymer is formed after 2.5 hours but conversion is only 72.6%. At 200° C., however, the polymer concentration remains low at slightly greater than 2% but the conversion approaches 90%. Thus, high isoprene conversion can be achieved by increasing temperature with little additional polymer formation.

EXAMPLE 3

A number of known polymerization inhibitors for styrene were compared with dinitrocresol for use as an inhibitor in the dimerization of isoprene. Each inhibitor was dissolved into freshly distilled isoprene in an amount to result in a concentration of $3 \times 10^{-3}$ molar in isoprene. The solution was charged to a one liter autoclave. The solution was flushed with nitrogen and heated to 175° C. The reaction time was 90 minutes. The autoclave was cooled and the reaction mixture was distilled at atmospheric pressure. Isoprene was collected at 32° C. and the dimer cut was collected at an overhead temperature of 160°-174° C. The fractions and pot residue were weighed and the isoprene weight was adjusted to reflect any shortage in the material balance. The effectiveness of the inhibitors in the isoprene dimerization reaction is listed in Table V.

TABLE V

Inhibitor Screening Study

| Inhibitor | % Isoprene Converted | Selectivity to Dimer | % Polymer |
|---|---|---|---|
| t-butyl catechol | 65.9 | 92.8 | 7.0 |
| Hydroquinone | 68.7 | 89.8 | 7.8 |
| 4-hydroxy TEMPO[1] | 67.9 | 89.1 | 7.4 |
| 4,6 dinitro-o-cresol | 67.8 | 97.2 | 1.8 |
| 2,6 dinitro-p-cresol | 65.9 | 97.6 | 1.5 |

[1]2,2,6,6-tetramethyl-4-piperidinol-1-oxyl.

As can be seen from Table V, the 4,6-dinitro-o-cresol and 2,6-dinitro-p-cresol significantly reduce the amount of polymer formation versus the other inhibitors. In addition, the selectivity to dimer remains high with the two dinitrocresols.

What is claimed is:

1. A process for the thermal dimerization of isoprene comprising heating isoprene at a temperature of from about 110° C. to about 250° C. in the presence of dinitrocresol.

2. A process for inhibiting polymerization reactions during the thermal dimerization of isoprene comprising heating isoprene at a temperature of from about 110° C. to about 250° C. in the presence of a sufficient amount of dinitrocresol to inhibit the polymerization of isoprene.

3. The process of claim 2 wherein the dinitrocresol is present in a concentration of from about 25 to about 3000 ppm.

4. The process of claim 3 wherein the dinitrocresol is present in a concentration of from about 100 to about 1000 ppm.

5. The process of claim 1 wherein the temperature ranges from about 150° C. to about 225° C.

6. The process of claim 1 wherein the dinitrocresol is selected from the group consisting of 3,5-dinitro-o-cresol, 4,6-dinitro-o-cresol and 2,6-dinitro-p-cresol.

7. The process of claim 6 wherein the dinitrocresol is 4,6-dinitro-o-cresol.

8. The process of claim 6 wherein the dinitrocresol is 2,6-dinitro-o-cresol.

9. A process from the preparation of limonene comprising the thermal dimerization of isoprene at a temperature from about 110° C. to about 250° C. in the presence of dinitrocresol.

10. The process of claim 1 wherein the thermal dimerization is conducted in a batchwise manner.

11. The process of claim 1 wherein the thermal dimerization is conducted in a semi-continuous manner.

12. The process of claim 1 wherein the thermal dimerization is conducted in a continuous manner.

* * * * *